United States Patent
Liu et al.

(10) Patent No.: US 9,194,856 B2
(45) Date of Patent: Nov. 24, 2015

(54) METHOD FOR DIAGNOSING CORROSION OF UNDERGROUND STORAGE TANK SYSTEM

(71) Applicant: INDUSTRIAL TECHNOLOGY RESEARCH INSTITUTE, Chutung, Hsinchu (TW)

(72) Inventors: Pang-Hung Liu, Taipei (TW); Huan-Yi Hung, Xiushui Township, Changhua County (TW); Chien-Wei Lu, Hsinchu (TW); Han-Wen Chu, Hsinchu (TW); You-Zung Hsieh, Taipei (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 205 days.

(21) Appl. No.: 13/938,921

(22) Filed: Jul. 10, 2013

(65) Prior Publication Data
US 2014/0170754 A1 Jun. 19, 2014

(30) Foreign Application Priority Data
Dec. 17, 2012 (TW) .............................. 101147894 A

(51) Int. Cl.
| | |
|---|---|
| *G01N 33/20* | (2006.01) |
| *G01N 17/00* | (2006.01) |
| *G01N 33/28* | (2006.01) |
| G01N 33/18 | (2006.01) |
| G01N 1/10 | (2006.01) |

(52) U.S. Cl.
CPC .............. *G01N 33/20* (2013.01); *G01N 17/006* (2013.01); *G01N 33/2835* (2013.01); *G01N 33/1813* (2013.01); *G01N 2001/1037* (2013.01)

(58) Field of Classification Search
CPC ...................................................... G01N 33/20
USPC ....................... 436/2–3, 6, 80–81, 84; 422/53
See application file for complete search history.

(56) References Cited

U.S. PATENT DOCUMENTS

| | | | | |
|---|---|---|---|---|
| 3,438,735 | A | * | 4/1969 | Doyle ............................. 436/60 |
| 3,981,584 | A | * | 9/1976 | Guymer ......................... 356/70 |

(Continued)

FOREIGN PATENT DOCUMENTS

| | | |
|---|---|---|
| CN | 102203219 | 9/2011 |
| EP | 0469772 | 2/1992 |

(Continued)

OTHER PUBLICATIONS

Onyeso C. C. Journal of ASTM International 2005, 2, 1-7.*

(Continued)

*Primary Examiner* — Arlen Soderquist
(74) *Attorney, Agent, or Firm* — Muncy, Geissler, Olds & Lowe, P.C.

(57) ABSTRACT method for diagnosing corrosion of an underground storage tank system is provided. The method includes the following steps. A sample from the underground storage tank system is collected, wherein the sample comprises at lease one metal ion. The species and the concentration of the metal ion in the sample are detected by an analysis instrument. A concentration threshold value is determined from a database according to the species of the metal ion. A mapping step is performed, wherein the concentration of the metal ion and the concentration threshold value are compared to diagnose if the underground storage tank system is corroded.

7 Claims, 3 Drawing Sheets

(56) References Cited

U.S. PATENT DOCUMENTS

| | | | |
|---|---|---|---|
| 4,169,677 A * | 10/1979 | Luria | 356/70 |
| 4,203,725 A * | 5/1980 | Snowden et al. | 436/60 |
| 4,238,197 A * | 12/1980 | Eisentraut et al. | 436/60 |
| 4,270,922 A * | 6/1981 | Kerfoot | 436/6 |
| 4,324,758 A * | 4/1982 | Eisentraut et al. | 422/430 |
| 4,448,887 A * | 5/1984 | Kauffman et al. | 436/60 |
| 4,672,366 A | 6/1987 | Butts | |
| 4,675,604 A | 6/1987 | Moyer et al. | |
| 5,236,845 A * | 8/1993 | Pierce et al. | 436/6 |
| 5,344,781 A | 9/1994 | Kitchen et al. | |
| 5,435,405 A | 7/1995 | Schempf et al. | |
| 5,586,161 A * | 12/1996 | Russell et al. | 378/45 |
| 5,757,419 A | 5/1998 | Qureshi et al. | |
| 5,898,002 A * | 4/1999 | Small | 436/6 |
| 6,104,970 A | 8/2000 | Schmidt, Jr. et al. | |
| 6,200,816 B1 * | 3/2001 | Farber et al. | 436/73 |
| 6,651,487 B1 * | 11/2003 | Petty | 73/61.46 |
| 6,691,557 B1 * | 2/2004 | Rice | 73/53.07 |
| 7,259,017 B2 * | 8/2007 | Kawabata et al. | 436/60 |
| 7,296,488 B2 | 11/2007 | Hock et al. | |
| 7,378,281 B2 * | 5/2008 | Morris et al. | 436/80 |
| 7,384,789 B2 * | 6/2008 | Banerjee et al. | 436/81 |
| 8,521,445 B2 * | 8/2013 | Snelling et al. | 702/34 |
| 2002/0187558 A1 * | 12/2002 | Bodkin et al. | 436/164 |
| 2003/0166292 A1 * | 9/2003 | Collins et al. | 436/80 |
| 2006/0270050 A1 * | 11/2006 | Naudts et al. | 436/84 |
| 2008/0116907 A1 | 5/2008 | Butler et al. | |
| 2008/0204274 A1 | 8/2008 | Peters | |
| 2010/0107741 A1 * | 5/2010 | Petty | 73/61.43 |
| 2011/0052447 A1 | 3/2011 | Roy et al. | |
| 2011/0066388 A1 * | 3/2011 | Snelling et al. | 702/30 |

FOREIGN PATENT DOCUMENTS

| | | |
|---|---|---|
| EP | 0469773 | 2/1992 |
| JP | 06341967 | 12/1994 |
| JP | 2005076070 | 3/2005 |
| JP | 2007271540 A | 10/2007 |
| TW | 381704 | 2/2000 |
| TW | 436617 | 5/2001 |
| TW | I381704 | 12/2007 |
| TW | 200841005 | 10/2008 |
| TW | 201202595 | 1/2012 |
| WO | WO 2007/033334 | 3/2007 |

OTHER PUBLICATIONS

Teixeira, L. S. G. et al, Talanta 2007, 72, 1073-1076.*
Korn, M. D. G. A. et al, Talanta 20074, 73, 1-11.*
Sousa, J. K. C. Fuel Processing Technology 2008, 89, 1180-1185.*
Jungers, R. H. et al, Environmental Health Perspectives 1975, 10, 143-150.*
de Campos, R. C. et al, Spectrochmica Acta Part B 2002, 57, 15-28.*
Roldan, P. S. et al, Fuel 2005, 84, 305-309.*
"Straight Talk on Tanks: Leak Detection Methods for Petroleum Underground Storage Tanks and Piping.", http://www.epa.gov/oust/pubs/index.htm, Sep. 2005, 32 pages, (EPA-510-B-5-001).
Bouyssiere et al., "Determination of mercury inorganic solvents and gas condensates by μflow-injection—inductively coupled plasma mass spectrometry using a modified total consumption micronebulizer fitted with single pass spray chamber.", Spectrochimica Acta Part B, 2006, pp. 1063-1068, vol. 61.
Bardal et al., "Corrosion Detection and Diagnosis", Aterials Science and Engineering, 2004, 23 pages.
Dicerbo et al., "Leak Detection for Tanks", DOE's Underground Storage Tank (UST) Leak Detection Workshop, Apr. 26, 1994, 29 pages.
Saint'Pierre, "Determination of Cd, Cu, Fe, Pb and Ti in gasoline as emulsion by electrothermal vaporization inductively coupled plasma mass spectrometry with analyte addition and isotope dilution calibration techniques", Spectrochimica Acta Part B, 2004, pp. 551-558, vol. 59.
Lienemann et al., "Trace Metal Analysis in Petroleum Products: Sample Introduction Evaluation in ICP-OES and Comparision with an ICP-MS Approach", Oil & Gas Science and Technology, 2007, pp. 69-77, vol. 62, No. 1.
Santelli et al., "Total sulfur determination in gasoline, kerosene and diesel fuel using inductively coupled plasma optical emission spectrometry after direct sample introduction as detergent emulsions", Spectrochimica Acta Part B, 2008, pp. 800-804, vol. 63.

* cited by examiner

METHOD FOR DIAGNOSING CORROSION OF UNDERGROUND STORAGE TANK SYSTEM

CROSS-REFERENCE TO RELATED APPLICATION

This application claims the benefit of Taiwan application Serial No. 101147894, filed Dec. 17, 2012, the disclosure of which is incorporated by reference herein in its entirety.

TECHNICAL FIELD

The disclosure relates to a method for diagnosing corrosion of an underground storage tank system, and particularly to a method for diagnosing corrosion of an underground storage tank system without requiring special detecting equipments operating inside the underground storage tank system.

BACKGROUND

An underground storage tank system includes an underground storage tank as well as underground pipes and adapters connected thereto. An underground storage tanks is defined as of which 10% or more of the total volume is buried underground, and such storage tank is used for storing oils, solvents, fuels, etc. In Taiwan, a majority of gas stations applies underground storage tanks to store gasoline and diesel fuel for sale, and fuels in gas stations are pumped via underground pipes from storage tanks to fuel dispensers. At present, about 90% of the storage tanks are made of steels, and about 60% of the underground pipes and adapters are made of metals in Taiwan. The gasoline and diesel fuel stored in the underground storage tanks in the gas stations are classified as contaminating materials according to the announcement by Environmental Protection Administration (EPA) in Taiwan. If the corrosion resistance treatment for the underground storage tank systems made of metals is poor, environmental pollution caused by the leakage of oils from corroded tanks may occur.

Current pollution control requires leakage detections of underground storage tank systems. The leakage detections include tightness test of tanks and pipes, inspection of organic vapor or floating oil in monitoring wells, and/or examination of soil contamination level by analysis instruments. As an abnormality is detected, the fuel has already leaked out of the underground storage tank system, and the leakage may have lasted for a certain period of time as detected, resulting serious pollution to the environment. To remedy leakage of petroleum products is a complicated process, which may include soil remediation and underwater remediation, of which the cost is huge, and more importantly, the damage to the environment is severe. Since gasoline and diesel duel contain a number of materials hazardous to human, once the gasoline or diesel fuel leakage occurs, the damaged caused is beyond estimation. However, the current leakage detection techniques of underground storage tank system either can only be done after gasoline or diesel has leaked or requires operating personnel getting into the tanks, which techniques are time-consuming, dangerous, and expensive.

Therefore, researchers have been working on developing new corrosion detection techniques to overcome the deficiencies of the current techniques.

A prior art disclosed a detection system for underground storage tank systems, incorporating a robot travelling the interior of a tank for performing the detection. However, the size of the robot restricts it from getting into underground pipes of the underground storage tank systems, therefore, only the corrosion information of the tank is provided. Hence, the corrosions of the pipes and adapters of the systems can not be detected according to the method. In addition, while the detection of a storage tank system is taking place, fuels cannot be provided by the storage tank system.

Another prior art disclosed an inspection apparatus for detecting defects, such as cracks, of pipes, which primarily utilizes optical fibers cooperating with image oscilloscopes and monitors, wherein the optical fiber image oscilloscopes extend into pipes to record images for detecting defects. However, the length of the optical fiber is limited, and the pipes may have corners which cannot be reached by the optical fiber; thus, the inspection apparatus cannot cover all sections of the pipes. In addition, the apparatus is merely for inspecting pipes, fuels cannot be provided from the pipes while the detection is taking place, and the inspecting process is time-consuming.

SUMMARY

According to an embodiment of the disclosure, a method for diagnosing corrosion of an underground storage tank system is provided. The method includes the following steps: collecting a sample from the underground storage tank system, wherein the sample comprises at least one metal ion; detecting the species and the concentration of the metal ion in the sample with an analysis instrument; determining a concentration threshold value from a database according to the species of the metal ion; and performing a mapping step, wherein the concentration of the metal ion and the concentration threshold value are compared to diagnose if the underground storage tank system is corroded.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
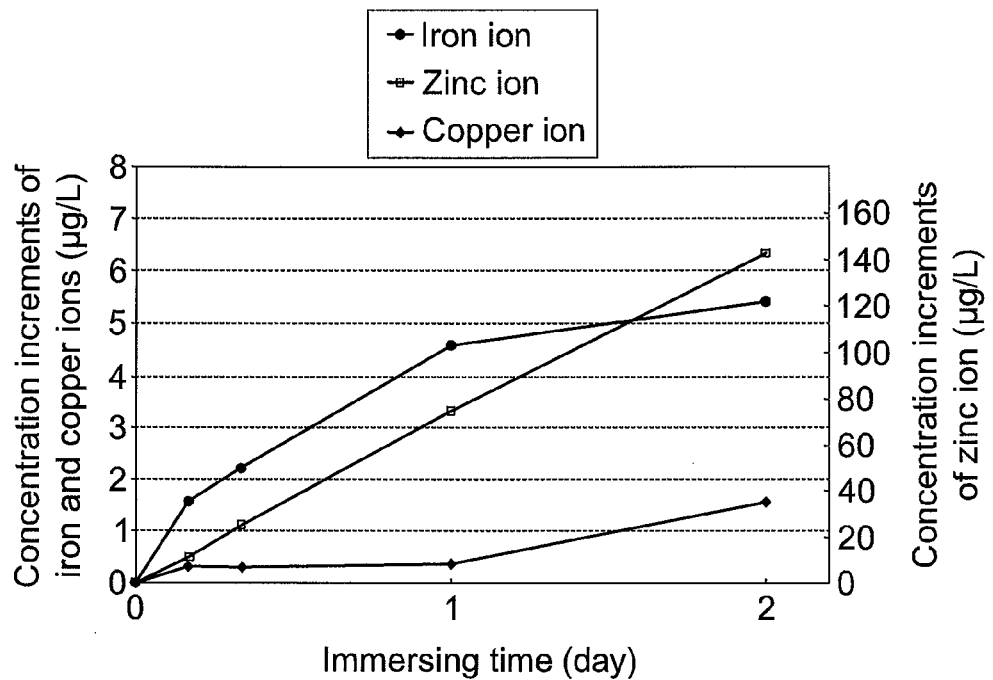
FIG. 1 shows the relationships between metal ion concentrations in the diesel fuel vs. immersing time of a section of a corroded zinc-coated steel pipe in the diesel fuel.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the embodiments of the disclosure, the species and concentration of at least one metal ion in a sample collected from an underground storage tank system are detected by an analysis instrument, thus, no special detecting equipment to be operated inside the underground storage tank system is required, the corrosion diagnosing time consumed is shortened, and the corrosion can be detected before the underground storage tank system is penetrated or cracked.

In the embodiments of the disclosure, a method for diagnosing corrosion of an underground storage tank system is provided. The following embodiments are for the purpose of elaboration only, not for limiting the scope of protection of the invention. Detailed structures and processes may be modified or changed by one having ordinary skill in the art after having the benefit of this description of the disclosure.

At first, a sample is collected from an underground storage tank system, and the sample comprises at least one metal ion. Next, the species and the concentration of the metal ion(s) are detected by an analysis instrument. Next, a concentration threshold value is determined from a database according to the species of the metal ion(s). For example, samples from a plurality of underground storage tank systems, which are free of corrosion concerns (uncorroded), are obtained in advance, and the species and the concentrations of the metal ions in the samples are detected. The species and the concentrations of the metal ions are stored in the database, followed by the determination of a concentration threshold value from the database according to the detected species and the concentrations of the metal ion(s) via a statistic calculation. Next, a mapping step is performed, wherein the concentration of the detected metal ion(s) and the corresponding concentration threshold value(s) are compared to diagnose if the underground storage tank system is corroded. It is to be noted that in the following description, when "a metal ion" or "the metal ion" is mentioned and described, it refers to at least one metal ion species; that is, such description indicates one or more metal ion species.

In the embodiment, when the underground storage tank system is corroded, the metal ion released from the rusting product, i.e. metal oxides, produced by the corroded region is dissolved into the sample. The species and the concentration of the metal ions in the sample, which is taken out from the underground storage tank system, are detected by an analysis instrument. As such, no special detecting equipment to be operated inside the underground storage tank system is required, the corrosion detection time consumed is shortened, and the corrosion can be detected before the leakage caused by penetration or cracking of corroded underground storage tank system.

In the embodiment, the underground storage tank system is diagnosed to be corroded when the detected concentration of the specific metal ion is higher than the corresponding concentration threshold value.

In the embodiment, the underground storage tank system may include an underground storage tank, at least a transport pipe, and at least an adapter, and the sample is stored in the underground storage tank. The sample passes through the transport pipe and the adapter before being collected. At least one of the underground storage tank, the transport pipe, or the adapter is diagnosed to be corroded when the concentration of the metal ion is higher than the concentration threshold value.

In the embodiment, the surface of the underground tank in contact with the sample contains a metal material; for example, the underground storage tank is a steel tank or a composite steel tank with an outer side covered by a protective layer. In the embodiment, the surface of the transport pipe in contact with the sample contains a metal material; for example, the transport pipe is a zinc-coated steel pipe or a seamless steel pipe. In the embodiment, the surface of the adapter in contact with the sample contains a metal material; for example, the adapter is a copper adapter. In the embodiment, the metal ion may include copper (Cu) ion, zinc (Zn) ion, iron (Fe) ion, or the combinations thereof. In one embodiment, the underground storage tank is an underground fuel tank, the transport pipe is a fuel pipe, and the adapter is a copper adapter. However, the selections of the types of the underground storage tank, the transport pipe, the adapter, and the liquid to be stored and transported may vary according to the conditions applied and are not limited thereto.

In the embodiment, the metal ion may be dissolved into the sample from the surface of the underground storage tank in contact with the sample. In the embodiment, the metal ion may be dissolved into the sample from the surface of the transport pipe in contact with the sample. In the embodiment, the metal ion may be dissolved into the sample from the surface of the adapter in contact with the sample. An underground storage tank system releases very little quantity of metal ion into the contacting sample when it is not corroded. As at least one of the underground storage tank, the transport pipe, or the adapter is corroded, the surface of the corroded region is oxidized, and hence the metal ion is released and dissolved into the sample. With the diagnosing method according to the embodiments of the disclosure, the concentration of the metal ion in the sample collected is detected by an analysis instrument, the corrosion detection time consumed is short, and the corrosion can be detected without having to detect the already leaked liquid or vaporized gas from the corroded and cracked underground storage tank system.

In the embodiment, the sample is collected from an outside output device connected to the underground storage tank, such that no special detecting equipment is required to be operated inside the underground storage tank system for detection, sampling is easy, the corrosion detection time consumed is shortened, and the cost of the corrosion detection is largely reduced. In the embodiment, the underground storage tank is such as a fuel tank, the transport pipe is such as a fuel pipe, the adapter is such as a copper adapter, and the output device is such as a fuel filling nozzle of a fuel dispenser. The sample (gasoline or diesel) is collected from the fuel filling nozzle.

In the embodiment, the transport pipe is such as an underground transport pipe. As the underground storage tank system is buried underground, the current method for detecting if at least one of the underground storage tank, the transport pipe, or the adapter is corroded is to detect if the liquid in the underground storage tank system is leaked to the exterior surrounding environment (e.g. the soil or underground water outside the underground storage tank system). For example, the underground storage tank is an underground fuel tank of a gas station, the transport pipe is an underground pipe of a gas station, and the adapter is an underground copper adapter. When the fuel is leaked, the surrounding soil and underground water is contaminated. Therefore, not only do the corroded underground fuel tank, the underground pipe, and the underground copper adapter need to be repaired and replaced, but the remediation of the soil and underground water also needs to be done, both of which are time-consuming, and the overall cost is very high as well. In contrast, according to the embodiments of the disclosure, the sample is collected through the outside output device, which is located aboveground and connected to the underground storage tank, from the underground storage tank system (e.g. the fuel is collected through the fuel filling nozzle of a fuel dispenser from the underground fuel tank). As such, sampling is easy, time consumed is less, and the corrosion can be detected before the underground storage tank system is penetrated and cracked by corrosion, providing a lower total cost of the corrosion detection.

Moreover, when a plurality of underground storage tanks are arranged in a single area (e.g. a plurality of underground fuel tanks are installed in one gas station), detection of a liquid leakage (fuel leakage) may only provides the information that at least one of the underground fuel tanks, and/or the underground transport pipes connected thereto, and/or the adapters thereof is corroded. A further detection step is required to clarify the exact corroded one(s) that need to be repaired and/or replaced. In contrast, according to the embodiments of the disclosure, each of the collected samples is corresponding to a specific group of an underground storage tank, corresponding underground transport pipe(s) and adapters. Therefore, the exact corroded one among many underground storage tanks, and/or the underground transport pipes connected thereto, and/or the adapters thereof can be detected and specified without any further detection steps, such that the overall cost of the corrosion repair is largely reduced.

In the embodiment, a chelating reagent may be further added into the sample stored in the underground storage tank prior to the collection of the sample, and the chelating reagent may form a metal complex with the metal ion. The original solubility of the metal oxide formed from the corrosion of the underground storage tank system in the sample is relatively low, and the addition of the chelating reagent in the sample can increase the solubility of the to-be-detected metal ion, such that the sensitivity of the corrosion detection is increased. In the embodiment, the concentration by weight of the chelating reagent in the sample is at an mg/L level, such as 0.1-1000 mg/L, but not limited thereto. In the embodiment, the metal ion is such as copper ion, zinc ion, or iron ion, and the chelating reagent is such as at least one of fatty acid methyl ester, diazo compound, or quinone compound. However, as long as the chelating reagent can react with the to-be-detected metal ion to form a metal complex dissolving in the sample, the selections of the chelating reagent may vary and depend on the conditions applied and are not limited to the above-mentioned examples.

In one embodiment, the underground storage tank is an underground fuel tank, the transport pipe is an underground pipe, the adapter is a copper adapter, and the chelating reagent is added in the underground fuel tank. As such, the metal ion produced from the metal oxide may react with the chelating reagent to form a metal complex, which is dissolved in the sample and can penetrate the filter of the fuel dispenser to be collected from the fuel filling nozzle.

Referring to FIG. 1, which shows the relationships between variations of metal ion concentrations in the diesel fuel vs. immersing time of a section of a corroded zinc-coated steel pipe in the diesel fuel. In the embodiment, a zinc-coated steel pipe is treated with salt spray to be rusted and oxidized, and then the rusted pipe is immersed in the diesel fuel. The diesel fuel contains 2 wt % of fatty acid methyl ester. As shown in FIG. 1, along with the increase of the immersing time of the rusted zinc-coated steel pipe in the diesel fuel, the concentrations of iron ion, copper ion, and zinc ion all increase significantly as well.

Figure 2A:
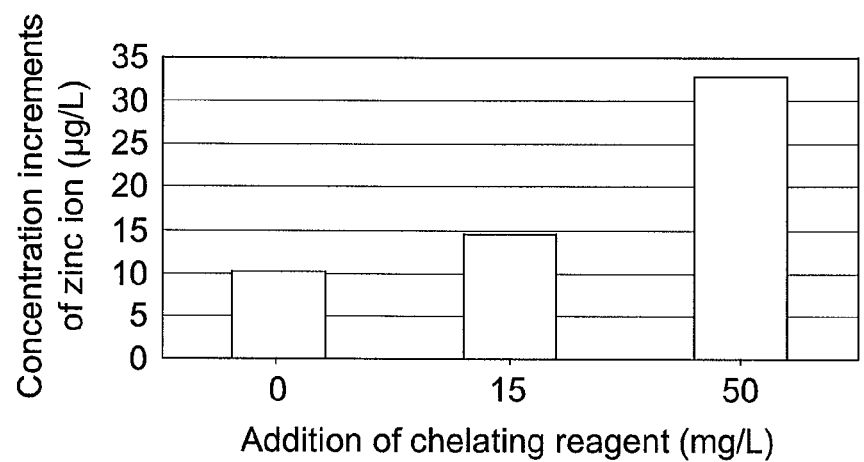
FIGS. 2A-2B show the relationships between zinc ion measured concentrations vs. amount of addition of the chelating reagents in gasoline #95.
Figure 2B:
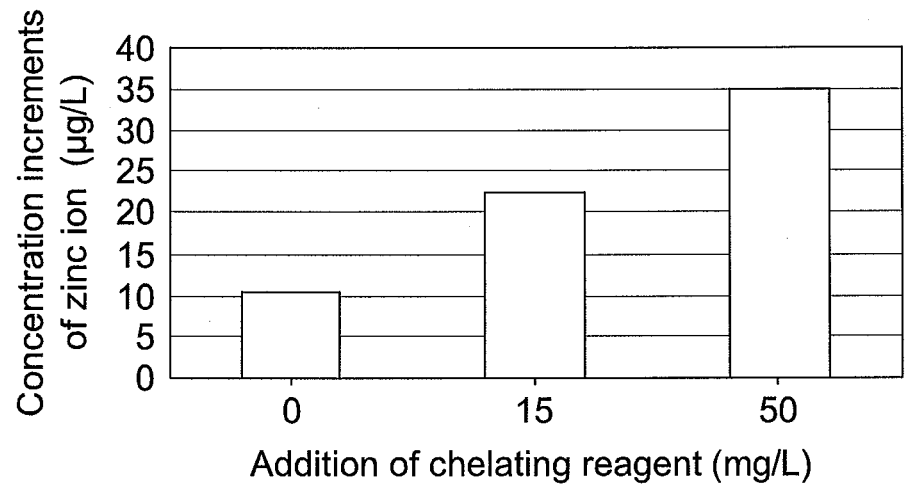

Referring to FIGS. 2A-2B, which show the relationships between zinc ion measured concentrations vs. amount of addition of the chelating reagents in gasoline #95 (gasoline #95 denotes the unleaded gasoline with a research octane number of 95). In the embodiment, a section of zinc-coated steel pipe is treated with salt spray to be rusted and oxidized, and then the rusted pipe is immersed in gasoline #95. In the embodiment as shown in FIG. 2A, a diazo compound chelating reagent is added; and in the embodiment as shown in FIG. 2B, a quinone compound chelating reagent is added. As shown in FIGS. 2A-2B, the more is the addition of the reagent, the higher is the concentration of the zinc ion measured. In other words, the addition of the chelating reagent can increase the detection sensitivity. In an embodiment, the amount of the addition of a chelating reagent is about, for example, 15-50 mg/L.

In the embodiment, the concentration threshold value of a measured metal ion is determined from the database according to the species of the metal ion.

In the embodiment, a plurality of concentration reference values are stored in the database, and the concentration reference values are the concentrations of the metal ion in samples collected from a plurality of uncorroded underground storage tank systems. In other words, a plurality of concentrations of the to-be-measured metal ion in samples collected from normal and uncorroded underground storage tank systems are stored in the database. In one embodiment, the underground storage tank is such as a fuel tank, and the species and the concentrations of the metal ion(s) in oils collected from uncorroded underground fuel tanks of a plurality of gas stations are stored in the database.

In the embodiment, the step of determining the concentration threshold value from the database according to the species of the metal ion comprises: obtaining the average value and the standard deviation of the concentration reference values of the metal ion; and determining the concentration threshold value according to the average value and the standard deviation of the concentration reference values. In the embodiment, the concentration threshold value is equal to, for example, the average value of the concentration reference values plus 2-6 times the standard deviation or 3-4 times the standard deviation. In one embodiment, the underground storage tank is such as an underground fuel tank, the concentration threshold value of the to-be-measured metal ion is the average value of the concentrations of the metal ion in oils, which are collected from a plurality of normal and uncorroded fuel tanks, plus 2-6 times the standard deviation or 3-4 times the standard deviation.

In the embodiment, the sensitivity of the analysis instrument to the metal ion is at a µg/L level. In the embodiment, the analysis instrument may be inductively coupled plasma mass spectrometer (ICP-MS), inductively coupled atomic emission spectrometer (ICP-AES), atomic absorption spectrometer (AA) or microwave plasma-atomic emission spectrometer (MP-AES). However, as long as the metal ion concentration can be detected and measured by the analysis instrument, the selection of the types of the analysis instrument may vary and depend on the actual condition applied and are not limited thereto.

Further explanation is provided with the following embodiments. In the following embodiments, the gas stations built in recent years in Taiwan are selected, from which the samples are collected and the species and concentrations of metal ions in gasoline and diesel fuels thereof are analyzed. The samples are classified into gasoline #92 (gasoline #92 denotes the unleaded gasoline with a research octane number of 92), gasoline #95, gasoline #98 (gasoline #98 denotes the unleaded gasoline with a research octane number of 98), and diesel fuel, and a database of metal ion concentrations from normal gas stations are built-up accordingly. In the embodiment, the concentrations of copper ion and zinc ion in gasoline are measured, and the concentrations of iron ion, copper ion, and zinc ion in diesel fuel are measured. Copper and iron ions come from the steel material of the fuel tanks and pipes and the copper adapters, and zinc ion comes from the coating material from the zinc-coated steel pipes.

In the embodiments, the concentrations of the metal ion in oils collected from fuel tanks of a plurality of normal gas stations, wherein no leakage observed in fuel tanks of the normal gas stations, and the corresponding concentration threshold values are presented in Tables 1-2. Table 1 shows the analytical results of concentrations obtained from the gasoline samples collected from the normal gas stations by ICP-MS, wherein the results for gasoline #92 and gasoline #95 are obtained from thirty normal gas stations, and the results for gasoline #98 are obtained from twenty-four normal gas stations. Table 2 shows the analytical results obtained from the diesel fuel samples collected from 18 normal gas stations by ICP-MS.

In the present embodiments, the concentration threshold value of a metal ion is equal to the average value of the metal ion concentrations obtained from a plurality of normal gas stations plus 3 times the standard deviation, with which the corrosion condition is diagnosed. However, the following examples are for purposes of describing particular embodiments only, and are not intended to be limiting.

TABLE 1

| | | | | Element (unit: μg/L) | |
|---|---|---|---|---|---|
| | | | | $^{63}Cu$ | $^{66}Zn$ |
| Gasoline | Unleaded | #92 | Average value | 1.49 | 2.64 |
| | | | Standard deviation | 0.88 | 1.76 |
| | | | Threshold value | 4.13 | 7.92 |
| | Unleaded | #95 | Average value | 0.68 | 2.48 |
| | | | Standard deviation | 0.54 | 1.18 |
| | | | Threshold value | 2.30 | 6.02 |
| | Unleaded | #98 | Average value | 1.69 | 2.84 |
| | | | Standard deviation | 1.21 | 2.24 |
| | | | Threshold value | 5.32 | 9.56 |

TABLE 2

| | Diesel fuel (unit: μg/L) | | |
|---|---|---|---|
| Element | Average value | Standard deviation | Threshold value |
| $^{56}Fe$ | 4.70 | 1.63 | 9.59 |
| $^{63}Cu$ | 0.95 | 0.53 | 2.54 |
| $^{66}Zn$ | 3.37 | 2.30 | 10.27 |

In addition, samples from another ten gas stations, that have been known to have fuel leakage problems causing environmental pollution, are collected and analyzed. The ten gas stations with fuel leakage problems are denoted as St1-St10. The analytical results of the oils collected from fuel tanks in the ten gas stations with leakage problems are compared with the average value of the concentrations obtained from the normal gas stations, as shown in FIGS. 3-5.

Figure 3:
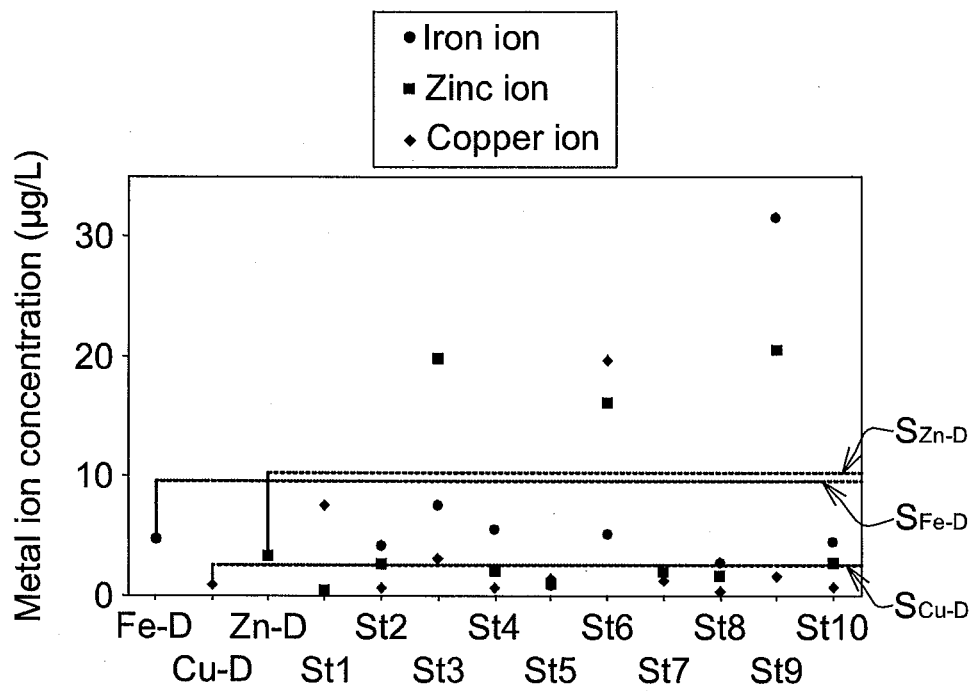
FIG. 3 shows the measured metal ion concentrations in diesel fuel obtained from gas stations St1-St10.

FIG. 3 shows the measured metal ion concentrations in diesel fuel obtained from gas stations St1-St10. Referring to FIG. 3, Fe-D represents the average value (4.7 μg/L, as shown in FIG. 2) of iron ion concentrations collected from the normal gas stations, Zn-D represents the average value (3.37 μg/L, as shown in FIG. 2) of zinc ion concentrations collected from the normal gas stations, and Cu-D represents the average value (0.95 μg/L, as shown in FIG. 2) of copper ion concentrations collected from the normal gas stations. Dashed lines $S_{Fe-D}$, $S_{Zn-D}$, and $S_{Cu-D}$ represent concentration threshold values of iron ion, zinc ion, and copper ion in diesel fuel, respectively; wherein in the present embodiments, the concentration threshold value of each metal ion is equal to the average value of concentrations of each metal ion collected from the normal gas stations plus 3 times the standard deviation.

As shown in FIG. 3, the iron ion concentration provided from gas station St9 is higher than the corresponding concentration threshold value, the zinc ion concentrations provided from gas stations St3, St6, and St9 are higher than the corresponding concentration threshold value, and the copper ion concentrations provided from gas stations St1, St3, and St6 are higher than the corresponding concentration threshold value. Accordingly, the fuel tank and/or pipe and/or adapter for diesel fuel in gas stations St1, St3, St6, and St9 are corroded.

Figure 4:
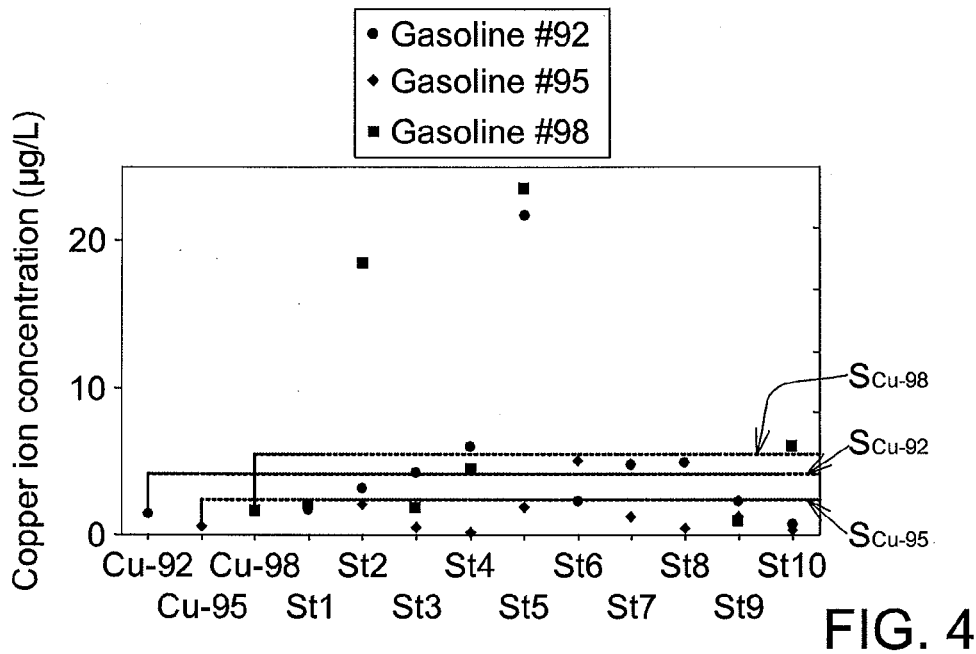
FIG. 4 shows the measured copper ion concentrations in gasoline obtained from gas stations St1-St10.
Figure 5:
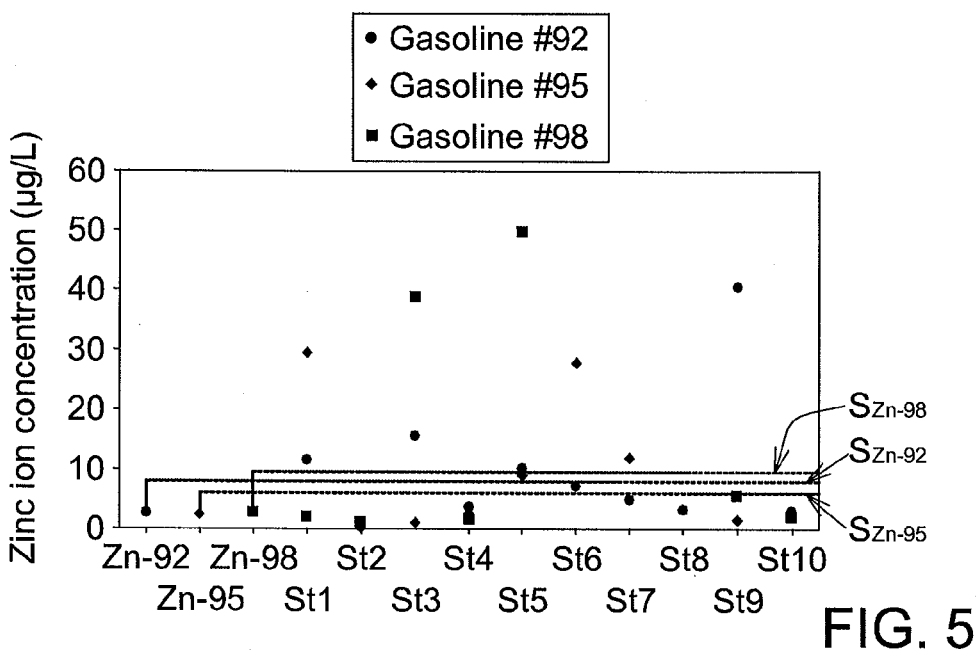
FIG. 5 shows the measured zinc ion concentrations in gasoline obtained from gas stations St1-St10.

FIG. 4 shows the measured copper ion concentrations in gasoline obtained from gas stations St1-St10. Referring to FIG. 4, Cu-92 represents the average value (1.49 μg/L, as shown in Table 1) of measured concentrations of copper ion in gasoline #92 collected from the normal gas stations, Cu-95 represents the average value (0.68 μg/L, as shown in Table 1) of measured concentrations of copper ion in gasoline #95 collected from the normal gas stations, and Cu-98 represents the average value (1.69 μg/L, as shown in Table 1) of measured concentrations of copper ion in gasoline #98 collected from the normal gas stations. Dashed lines $S_{Cu-92}$, $S_{Cu-95}$, and $S_{Cu-98}$ represent concentration threshold values of copper ions in gasoline #92, gasoline #95, and gasoline #98, respectively; wherein in the present embodiments, the concentration threshold value of copper ion in each gasoline is equal to the average value of concentrations of copper ion collected from the normal gas stations, for each gasoline, plus 3 times the standard deviation.

As shown in FIG. 4, the copper ion concentrations in gasoline #92 provided by gas stations St3-St5 and St7-St8 are higher than the corresponding concentration threshold value, the copper ion concentration in gasoline #95 provided by gas station St6 is higher than the corresponding concentration threshold value, and the copper ion concentrations in gasoline #98 provided by gas stations St2, St5, and St10 are higher than the corresponding concentration threshold value. Accordingly, the fuel tank and/or pipe and/or adapter for gasoline #92 in gas stations St3-St5 and St7-St8 are corroded, the fuel tank and/or pipe and/or adapter for gasoline #95 in gas station St6 are corroded, and the fuel tank and/or pipe and/or adapter for gasoline #98 in gas stations St2, St5, and St10 are corroded.

FIG. 5 shows the measured zinc ion concentrations in gasoline obtained from gas stations St1-St10. Referring to FIG. 5, Zn-92 represents the average value (2.64 μg/L, as shown in Table 1) of measured concentrations of copper ion in gasoline #92 collected from the normal gas stations, Zn-95 represents the average value (2.48 μg/L, as shown in Table 1) of measured concentrations of zinc ion in gasoline #95 collected from the normal gas stations, and Zn-98 represents the average value (2.84 μg/L, as shown in Table 1) of measured concentrations of zinc ion in gasoline #98 collected from the normal gas stations. Dashed lines $S_{Zn-92}$, $S_{Zn-95}$, and $S_{Zn-98}$ represent concentration threshold values of zinc ions in gasoline #92, gasoline #95, and gasoline #98, respectively; wherein in the present embodiments, the concentration threshold value of zinc ion in each gasoline is equal to the average value of concentrations of zinc ion collected from the normal gas stations, for each gasoline, plus 3 times the standard deviation.

As shown in FIG. 5, the zinc ion concentrations in gasoline #92 provided by gas stations St1, St3, St5, and St9 are higher than the corresponding concentration threshold value, the zinc ion concentrations in gasoline #95 provided by gas stations St1 and St5-St7 are higher than the corresponding concentration threshold value, and the copper ion concentrations in gasoline #98 provided by gas stations St3 and St5 are higher than the corresponding concentration threshold value. Accordingly, the fuel tank and/or pipe and/or adapter for gasoline #92 in gas stations St1, St3, St5, and St9 are corroded, the fuel tank and/or pipe and/or adapter for gasoline #95 in gas stations St1 and St5-St7 are corroded, and the fuel tank and/or pipe and/or adapter for gasoline #98 in gas stations St3 and St5 are corroded.

In the embodiments of the present disclosure, as shown in FIGS. 3-5, each sample is corresponding to a specific group of an underground storage tank, an underground transport pipe, and an adapter. Therefore, according to the diagnosing method of the present disclosure, the corrosion can be detected before the leakage and crack of the underground storage tank and/or the transport pipe connected thereto and/or the adapter thereof occur. Furthermore, the corroded underground storage tank and/or the transport pipe connected thereto and/or the adapters thereof, that need to be repaired and replaced, can be specified precisely without requiring additional detection steps. As such, the overall cost of the corrosion detection and remediation is largely reduced.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for diagnosing corrosion of an underground storage tank system, comprising:
    collecting a sample from the underground storage tank system, wherein the sample comprises at least one metal ion, and the at least one metal ion is copper (Cu) ion, zinc (Zn) ion, iron (Fe) ion, or combinations thereof;
    detecting the species and the concentration of the metal ion in the sample by an analysis instrument;
    determining a concentration threshold value from a database according to the species of the metal ion by a processor, wherein a plurality of concentration reference values are stored in the database, and the concentration reference values are the concentrations of the metal ion in a plurality of samples collected from a plurality of uncorroded underground storage tank systems, determining the concentration threshold value comprising:
        obtaining the average value and the standard deviation of the concentration reference values; and
        determining the concentration threshold value according to the average value and the standard deviation of the concentration reference values, wherein the concentration threshold value is the average value plus 2-6 times the standard deviation; and
    performing a mapping step by the processor, wherein the concentration of the metal ion and the concentration threshold value are compared to diagnose if the underground storage tank system is corroded, and the underground storage tank system is determined to be corroded when the concentration of the metal ion is higher than the concentration threshold value.

2. The method for diagnosing corrosion of the underground storage tank system according to claim 1, wherein the metal ion is dissolved into the sample from a surface of the underground storage tank system in contact with the sample.

3. The method for diagnosing corrosion of the underground storage tank system according to claim 1, wherein the underground storage tank system comprises an underground storage tank, at least a transport pipe, and at least an adapter, the sample passes through the transport pipe and the adapter before being collected, and at least one of the underground storage tank, the transport pipe, or the adapter is corroded when the concentration of the metal ion is higher than the concentration threshold value.

4. The method for diagnosing corrosion of the underground storage tank system according to claim 3, wherein the metal ion is dissolved into the sample from a surface of the transport pipe in contact with the sample.

5. The method for diagnosing corrosion of the underground storage tank system according to claim 1, further comprising:
    adding a chelating reagent into the sample in the underground storage tank system.

6. The method for diagnosing corrosion of the underground storage tank system according to claim 5, wherein the chelating reagent is dissolved into the sample and forms a metal complex with the metal ion.

7. The method for diagnosing corrosion of the underground storage tank system according to claim 1, wherein the analysis instrument is inductively coupled plasma mass spectrometer (ICP-MS), inductively coupled atomic emission spectrometer (ICP-AES), atomic absorption spectrometer (AA), or microwave plasma-atomic emission spectrometer (MP-AES).

* * * * *